(12) United States Patent
Schrott et al.

(10) Patent No.: US 11,857,662 B2
(45) Date of Patent: Jan. 2, 2024

(54) HAIR COLORING COMPOSITIONS AND METHODS THEREOF

(71) Applicant: KAO USA INC., Cincinnati, OH (US)

(72) Inventors: Adam Schrott, Hebron, KY (US); Chris Owens, Ft. Thomas, KY (US); Vincent Fischer, Saint Petersburg, FL (US)

(73) Assignee: KAO USA INC., Cincinnati, OH (US)

( * ) Notice: Subject to any disclaimer, the term of this patent is extended or adjusted under 35 U.S.C. 154(b) by 212 days.

(21) Appl. No.: 17/141,003

(22) Filed: Jan. 4, 2021

(65) Prior Publication Data

US 2021/0145724 A1 May 20, 2021

Related U.S. Application Data

(63) Continuation of application No. 15/887,327, filed on Feb. 2, 2018, now abandoned.

(51) Int. Cl.

| A61K 8/60 | (2006.01) |
|---|---|
| A61K 8/49 | (2006.01) |
| A61Q 5/10 | (2006.01) |
| A61K 8/35 | (2006.01) |
| A61Q 5/06 | (2006.01) |
| A61K 8/04 | (2006.01) |
| A61K 8/34 | (2006.01) |
| A45D 19/00 | (2006.01) |

(52) U.S. Cl.
CPC ............... *A61K 8/60* (2013.01); *A61K 8/046* (2013.01); *A61K 8/342* (2013.01); *A61K 8/345* (2013.01); *A61K 8/35* (2013.01); *A61K 8/4973* (2013.01); *A61K 8/604* (2013.01); *A61Q 5/065* (2013.01); *A61Q 5/10* (2013.01); *A45D 19/0066* (2021.01); *A45D 2200/155* (2013.01)

(58) Field of Classification Search
None
See application file for complete search history.

(56) References Cited

U.S. PATENT DOCUMENTS

| 6,231,837 B1 * | 5/2001 | Stroud ................... A61K 8/345 424/59 |
|---|---|---|
| 8,974,548 B2 | 3/2015 | Wang et al. |
| 2005/0210606 A1 | 9/2005 | Wilz |
| 2005/0244349 A1 | 11/2005 | Chaudhuri et al. |
| 2006/0005326 A1 | 1/2006 | Rollat-Corvol et al. |
| 2008/0279796 A1 * | 11/2008 | Handrosch ............ C09C 1/0021 106/419 |
| 2009/0126755 A1 | 5/2009 | Guerin et al. |
| 2012/0102662 A1 | 5/2012 | Wood et al. |
| 2015/0064124 A1 | 3/2015 | Yontz et al. |

FOREIGN PATENT DOCUMENTS

| DE | 10 2007 042 286 A1 | 3/2009 |
|---|---|---|
| DE | 102011017519 A1 | 10/2012 |
| EP | 1 591 099 A2 | 11/2005 |
| EP | 1 970 414 A2 | 9/2008 |
| EP | 3 034 065 A1 | 6/2016 |
| GB | 953170 A | 3/1964 |

OTHER PUBLICATIONS

English translation of DE102007042286(2023).*
Archived Novaphene web product page for dimethyl isosorbide (Jan. 28, 2014). Obtained from <https://web.archive.org/web/20140128094013/http://www.novaphene.com/novasolve.aspx.htm>.*
European Office Action dated Aug. 11, 2020 in Patent Application No. 19 154 882.5, 3 pages.
European Office Action dated Apr. 24, 2020, in Patent Application No. 19 154 882.5.
"Airbrush Instant Self-Tan", Database GNPD [Online] Mintel, XP055658865, Mar. 2010, 5 pages.
Extended European Search Report dated Apr. 25, 2019 in Patent Application No. 19154882.5.
"Ready to Wear Tan 5 Minute Mousse", Database GNPD [Online] Mintel; XP002790426, Mar. 2, 2015, 6 pages.
"Make Up Tint", Database GNPD [Online] Mintel; XP002790427, Nov. 17, 2017, 3 pages.
"Color Cream", Database GNPD [Online] Mintel; XP002790428, Jun. 2, 2014, 7 pages.

* cited by examiner

*Primary Examiner* — Patricia Duffy
*Assistant Examiner* — Garen Gotfredson
(74) *Attorney, Agent, or Firm* — Oblon, McClelland, Maier & Neustadt, L.L.P.

(57) ABSTRACT

A hair coloring composition that includes about 5 to 25 wt. % of a first monosaccharide having 2 to 4 carbon atoms, up to about 10 wt. % of a second monosaccharide having 2 to 4 carbon atoms, about 0.1 to 5 wt. % of a surfactant, and about 0.1 to 5 wt. % of a delivery agent, each based on a total weight of the hair coloring composition. A method for coloring hair, that involves applying the hair coloring composition onto the hair, and optionally applying heat to the hair at a dyeing temperature of 30 to 205° C.

19 Claims, No Drawings

HAIR COLORING COMPOSITIONS AND METHODS THEREOF

BACKGROUND OF THE INVENTION

Field of the Invention

The present invention relates to hair coloring compositions and methods of coloring hair using the hair coloring compositions.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

The appearance of gray hair typically begins around the age of 30 and is a top hair care concern for both men and women. Graying hair may lead to an emotional reaction including feelings of loss of strength, loss of youthfulness, and loss of vitality, particularly so for women with graying hair. Therefore many consumers choose to cover up gray hair by full coverage hair dyes or by blending of gray hairs into naturally pigmented hair.

In attempts to cover gray hair, some consumers select box colors or do-it-yourself sprays because such systems can be applied at home. However, technology limitations often make the resulting dyed hair appear flat or without preferred multi-tones, resulting in an unnatural look. Moreover, such box colors or spray systems can be difficult to apply and may result in unwanted staining of the scalp.

The use of salon services, while generally providing a more natural looking, multi-tonal coloration, can be cost and time prohibitive for many consumers and is perceived to cause hair damage due to repeated and prolonged exposure to chemical treatments.

Further, many consumers are generally skeptical of hair dyes due to the perceived effects of harsh chemicals, such as oxidizing agents, on hair structure and general follicle health.

In view of the forgoing, there is a need for a hair coloring composition that can be easily applied at home in a consumer friendly amount of time for providing long lasting, deep, rich, multi-tonal, natural-looking dyed hair without the use of harsh treatment chemicals (e.g., oxidizing agents) or staining of the scalp.

SUMMARY OF THE INVENTION

Accordingly, it is one object of the present invention to provide novel hair coloring compositions.

It is another object of the present disclosure to provide novel methods for coloring hair by applying the hair coloring compositions onto the hair.

These and other objects, which will become apparent during the following detailed description, have been achieved by the inventors' discovery that the following hair coloring compositions can be easily applied at home with short application times to provide a deep, rich, long lasting, multi-tonal color, while minimizing staining of the scalp and without the use of harsh oxidizing agents.

Thus, the present invention provides:

(1) A hair coloring composition, comprising:
about 5 to 25 wt. % of a first monosaccharide having 2 to 4 carbon atoms;
up to about 10 wt. % of a second monosaccharide having 2 to 4 carbon atoms;
about 0.1 to 5 wt. % of a surfactant; and
about 0.1 to 5 wt. % of a delivery agent, each based on a total weight of the hair coloring composition.

(2) The hair coloring composition of (1), wherein the first monosaccharide is dihydroxyacetone.

(3) The hair coloring composition of (1), wherein the second monosaccharide is erythrulose.

(4) The hair coloring composition of (1), which has about 5 to 10 wt. % of the first monosaccharide and about 0.001 to 1 wt. % of the second monosaccharide, each based on a total weight of the hair coloring composition.

(5) The hair coloring composition of (1), wherein a weight ratio of the first monosaccharide to the second monosaccharide is 10:1 to 1,000:1.

(6) The hair coloring composition of (1), wherein the surfactant is at least one nonionic surfactant selected from the group consisting of an alkyl pyranoside and a polyoxyalkylene ether of a fatty alcohol.

(7) The hair coloring composition of (1), wherein the surfactant is a mixture of decyl glucoside and ceteareth-25.

(8) The hair coloring composition of (1), wherein the delivery agent is a dianhydrohexitol, a $C_1$ to $C_4$ monoalkoxy substituted dianhydrohexitol, or a $C_1$ to $C_4$ dialkoxy substituted dianhydrohexitol.

(9) The hair coloring composition of (1), wherein the delivery agent is dimethyl isosorbide.

(10) The hair coloring composition of (1), further comprising
about 60 to 90 wt. % of water, and
about 0.5 to 5 wt. % of an organic solvent, each based on a total weight of the hair coloring composition.

(11) The hair coloring composition of (1), further comprising at least one of the following additives:
up to about 3 wt. % of a preservative,
up to about 3 wt. % of an acidulant,
about 1 to 10 wt. % of a conditioning agent, and
up to about 1 wt. % of a fragrance, each based on a total weight of the hair coloring composition.

(12) The hair coloring composition of (1), which has a pH of about 2 to 5.

(13) The hair coloring composition of (11), wherein the conditioning agent is present, and is glycerin.

(14) The hair coloring composition of (1), which is in the form of a foam.

(15) A method for coloring hair, comprising:
applying the hair coloring composition of (1) onto the hair.

(16) The method of (15), further comprising applying heat to the hair at a dyeing temperature of 30 to 205° C.

(17) The method of (16), wherein the dyeing temperature is 30 to 60° C.

(18) The method of (16), wherein the dyeing temperature is more than 60° C. and up to 205° C.

(19) The method of (15), wherein the hair coloring composition is in the form of a foam.

(20) The method of (15), wherein the hair coloring composition is not applied to skin.

The foregoing paragraphs have been provided by way of general introduction, and are not intended to limit the scope of the following claims. The described embodiments, together with further advantages, will be best understood by reference to the following detailed description.

DETAILED DESCRIPTION OF THE INVENTION

In the following description, it is understood that other embodiments may be utilized and structural and operational changes may be made without departure from the scope of the present embodiments disclosed herein.

Definitions

As used herein, the term "fatty" describes a long-chain hydrophobic portion of a compound made up of hydrogen and anywhere from 6 to 26 carbon atoms, which may be fully saturated or partially unsaturated, and optionally attached to a functional group such as a hydroxyl group or a carboxyl group. Fatty alcohols, fatty acids, fatty esters, fatty amides, and fatty hydrocarbon oils are examples of materials which contain a fatty portion. When the material contains a carbon-containing functional group, as is the case in a fatty acid which contains a carboxylic acid group (—COOH), the 6 to 26 carbon count refers to only the hydrophobic portion attached to the carbon-containing function group. Therefore, stearic acid, which has 18 carbons total, has a fatty portion with 17 carbon atoms.

As used herein, "polyoxyalkylene" describes a polyether group derived from polymerization of one or more alkylene oxides having 2 to 4 carbon atoms, and specifically includes polyoxyethylene (derived from ethylene oxide), polyoxypropylene (derived from propylene oxide), and polyoxybutylene (derived from butylene oxide), as well as mixtures thereof.

When referencing hair coloring compositions, the phrase "substantially free", unless otherwise specified, describes an amount of a particular component present in the hair coloring composition being less than about 1 wt. %, preferably less than about 0.5 wt. %, more preferably less than about 0.1 wt. %, even more preferably less than about 0.05 wt. %, yet even more preferably 0 wt. %, relative to a total weight of the hair coloring composition.

As used herein, the terms "optional" or "optionally" means that the subsequently described event(s) can or cannot occur or the subsequently described component(s) may or may not be present (e.g., 0 wt. %).

Various hair coloring composition ingredients are listed throughout the present disclosure and are organized according to their primary or most desired function, benefit, or use. However, categorization of an ingredient under a particular function, benefit, or use is not meant to limit that ingredient to only that function, benefit, or use. For example, listing of benzyl alcohol as a preservative does not limit the usefulness of benzyl alcohol to only that of a preservative, since benzyl alcohol can also impart other beneficial attributes, such as acting as a fragrance and/or a solvent.

When referencing "hair" or "keratin fibers" herein, it is to be recognized that hair exists on many different mammals (e.g., human) on many different body parts, and application of the hair coloring compositions herein is not limited to hair found on a specific body part. For example, the hair coloring compositions may be applied for dyeing of hair found on the head/scalp including the crown and side of the head, facial hair, and the like. Preferably, the hair being dyed is located on the head or scalp.

Hair Coloring Composition

The present disclosure is directed to hair coloring compositions that are substantially free of, preferably completely free of (0 wt. %) harsh oxidizing agents, are easy to apply without staining the scalp, and that provide rich, multi-tonal, natural-looking dyed hair. The hair coloring compositions may be used to dye hair of any color to a different shade or color, or preferably to restore gray hair to an original hair color, for example, yellow or brown.

The hair coloring compositions therefore contain components which enable dyeing of keratin fibers without damaging the keratin fibers, as well as components which facilitate delivery of active ingredients and allow the hair coloring compositions to be easily applied at home to provide natural looking dyed hair. Such compositions generally include the following components: a dyestuff, which is preferably a mixture monosaccharides having 2 to 4 carbon atoms, a surfactant, a delivery agent, and optionally water, an organic solvent, a preservative, an acidulant, a conditioning agent, and a fragrance. In preferred embodiments, all components are compatible with the dyestuff (i.e., do not react with or cause the dyestuff to react) and are homogeneously dispersed or dissolved uniformly throughout the hair coloring composition.

The hair coloring composition may be in a form chosen from a liquid, a solution, an emulsion, a cream, a gel, a paste, a mousse, a foam, or any other form that is suitable for topical application to keratin fibers. Preferably, the hair coloring composition is in the form of a foam, and is therefore easy to apply to hair follicles, including hair follicle roots, while minimizing contact with the scalp to avoid staining of the skin.

Dyestuff

To act as an effective hair dye (e.g., for gray hair), the hair coloring composition herein includes a "dyestuff", which is any colored molecule that, when it is brought into contact with the keratin material, colors this material, or any non-colored molecule that, in contact with the keratin material, reacts with and colors the keratin material without the aid of an additional chemical agent, for example, without the aid of an oxidizing agent.

The amount of dyestuff present in the hair coloring composition may vary depending on the color shade desired and the quantity and nature of the other components, however, the dyestuff is typically present in amounts of at least about 1 wt. %, preferably at least about 2 wt. %, more preferably at least about 3 wt. %, even more preferably at least about 4 wt. %, yet even more preferably at least about 5 wt. %, and up to about 35 wt. %, preferably up to about 25 wt. %, preferably up to about 20 wt. %, preferably up to about 15 wt. %, preferably up to about 10 wt. %, more preferably up to about 8 wt. %, even more preferably up to about 7 wt. %, yet even more preferably up to about 6 wt. %, based on a total weight of the hair coloring composition.

In preferred embodiments, the dyestuff is a monosaccharide. Monosaccharides, such as dihydroxyacetone, react with amino acids naturally occurring in keratin materials and, by virtue of a Maillard reaction, form melanoids which produce a color change to the keratin material (Bobin et al. J. Soc. Cosmet. Chem., 35 pages 265-272, 1984; Maillard L. C., C. R. Acad. Sci. 154, 66-68, 1912—each incorporated herein by reference in its entirety). Advantageously, such color change is produced without the need for additional chemical agents (e.g., oxidizing agents) to drive the reaction. Different amino acids react with different monosaccharides differently to produce a variety of tones of coloration from yellow to brown. Any monosaccharide capable of reacting with amino acids found in keratin fibers (e.g., naturally occurring amino acids) to produce a colored keratin material, can be employed as the dyestuff herein. The monosaccharide may be an aldose having 2 to 6 carbon atoms, preferably 3 to 5 carbon atoms, more preferably 3 to 4 carbon atoms, even more preferably 3 carbon atoms, a ketose having 3 to 6 carbon atoms, preferably 4 to 5 carbon atoms, more preferably 3 to 4 carbon atoms, including mixtures such aldoses and/or ketoses. Exemplary monosaccharides include, but are not limited to, glycolaldehyde, glyceraldehyde, dihydroxyacetone (DHA), erythrulose, meso-tartaric aldehyde, glucose, gulose, xylose, fructose, ribose, arabinose, allose, talose, altrose, idose, mannose, galactose, and erythrose. Such monosaccharides produce natural looking color shades when applied to hair owing at least partially to the multi-tone color variations produced by reaction with various amino acids. Further advantages of employing monosaccharides as the dyestuff component herein, is that the monosaccharides are derivatives of, or are closely related to, physiologically harmless naturally occurring vegetable compounds, and the colors produced are integral with the keratin fibers themselves (Maillard reaction products) and are thus resistant to washing.

In preferred embodiments, a mixture of monosaccharides is used, for example a mixture of a first monosaccharide and a second monosaccharide which is different from the first monosaccharide. The first monosaccharide is preferably a ketose having 2 to 4 carbon atoms, preferably three carbon atoms. In preferred embodiments, the first monosaccharide is dihydroxyacetone. The first monosaccharide may be present in amounts of from about 5 wt. %, preferably from about 5.5 wt. %, more preferably from about 6 wt. %, even more preferably from about 6.5 wt. %, and up to about 25 wt. %, preferably up to about 20 wt. %, preferably up to about 15 wt. %, preferably up to about 10 wt. %, more preferably up to about 9 wt. %, even more preferably up to about 8 wt. %, yet even more preferably up to about 7 wt. %, based on the total weight of the hair coloring composition. The second monosaccharide is preferably a ketose having 2 to 4 carbon atoms, preferably four carbon atoms. In preferred embodiments, the second monosaccharide is erythrulose. The second monosaccharide may be present in amounts of from about 0.001 wt. %, preferably from about 0.01 wt. %, more preferably from about 0.1 wt. %, even more preferably from about 0.5 wt. %, and up to about 10 wt. %, preferably up to about 8 wt. %, preferably up to about 6 wt. %, preferably up to about 4 wt. %, more preferably up to about 3 wt. %, even more preferably up to about 2 wt. %, yet even more preferably up to about 1 wt. %, based on the total weight of the hair coloring composition.

The inventors have unexpectedly found that use of a single monosaccharide (e.g., dihydroxyacetone) often produces an unnatural dye result, for example an orange tone, but that a mixture of monosaccharides (e.g., dihydroxyacetone and erythrulose) provides a rich, long lasting dye with natural-looking multi-tonal colors.

While the weight ratio of the first monosaccharide (e.g., dihydroxyacetone) to the second monosaccharide (e.g., erythrulose) may be varied depending on color shade, and the desired length of coloration, the weight ratio is typically from 10:1, preferably from 50:1, preferably from 100:1, preferably from 200:1, preferably from 300:1, more preferably from 400:1, even more preferably from 500:1, yet even more preferably from 600:1, and up to 1,000:1, preferably up to 900:1, more preferably up to 800:1, even more preferably up to 700:1.

In preferred embodiments, the hair coloring compositions are substantially free of dyestuffs other monosaccharides, which includes being substantially free of, preferably completely free of (i.e., 0 wt. %) acid dyes, decoctions or extracts, direct dyes, and/or pigments which provide color. Alternatively, the hair coloring compositions may include other dyestuffs such as acid dyes, decoctions or extracts, direct dyes, and/or pigments in amounts listed previously.

Examples of acid dyes which may be useful dyestuffs include, but are not limited to, Yellow No. 203 (D&C Yellow No. 10, color index (CI) given as CI 47005), Orange No. 205 (D&C Orange No. 4, CI 15510), Red No. 227 (D&C Red No. 33, CI 17200), Violet No. 401 (Ext. D&C Violet No. 2, CI 07301), and Black No. 401, CI 20470). Combinations of these acid dyes can be used, for example, Orange 4+ Yellow 10+ External Violet 2, Orange 4+ Red 33+ External Violet 2, Orange 4+ Red 33+ External Violet 2, or Orange 4+ Red 3.

Extracts or decoctions may also be employed herein as dyestuffs, and are preferably extracts or decoctions from plant sources, for example, henna-based extracts, melanin, curcumin, caramels, malva extracts, hibiscus extracts, green teas, ginsengs, annattos, beta-carotenes, walnut extracts (e.g., black walnut), *Menthe piperta, Melva silvestris, Cynara Scolymus, Theasinensis, Juglans regia, Lawsonia inermis, Castanea vulgaris, Asorum europaeum, Leonurus cardiac, Ballotafoetida, Ocimum basilicum, Stachys officinalis, Brunella vulgaris, Calamintha officinalis, Thymus vulgaris, Rosmarinus officinalis, Humulus lupulus, Vaccinium myrtillus, Arctotaphylosuva-ursi, Calluna vulgaris, Artemisian abisinthium, Artemisia vulgaris, Artemisia abrotonum, Artemisia glacialis, Artimesia mutellina, Artemisia spicata, Chamamelum nobile, Fraxinus excelsior, Syringa vulgaris, Jasminium grandijlorum, Lythrum salicaria, Althaea officinalis, Hysopus officinalis, Origanum majorana, Salvia officinalis, Melissa officinalis, Melittis melissophylum, Lavandula officinalis, Quercus robur, Fagus sylvatica, Nepta cataria, Origanum dictamus, Thymus serpyllum, Cichorium intybus* L., and *Gymnema sylvestre*.

The hair coloring composition may include direct dyes as the dyestuff component. Various classes of direct dyes may be employed, such as indole-based dyes (e.g., isatin, 5,6-dihydroxy indole, indigo); pyrimidine-based dyes (e.g., alloxan); indane-based dyes (e.g., ninhydrin); nitrobenzene-based dyes (e.g., 1,4-diamino-2-nitrobenzene, 1-amino-2-nitro-4-β-hydroxyethylaminobenzene, 1-amino-2-nitro-4-bis(β-hydroxyethyl)aminobenzene, 1,4-bis(β-hydroxyethylamino)-2-nitrobenzene, 1,2-diamino-4-nitrobenzene, or the corresponding nitropyridine variants); quinone-based dyes (e.g., anthraquinone, 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone, lawsone, juglone, alizarin, purpurin, carminic acid, kermesic acid, spinulosin, Disperse Red 15, Solvent Violet 13, Disperse Violet 1, Disperse Violet 4, Disperse Blue 1, Disperse Violet 8, Disperse Blue 3, Disperse Red 11, Disperse Blue 7, Basic Blue 22, Disperse Violet 15, Basic Blue 99); azo-based dyes (e.g., 1,3-dimethyl-2-[[4-(dimethylamino)phenyl]azo]-1H-imidazolium chloride, 1,3-dimethyl-2-[(4-aminophenyl)azo]-1H-imidazolium chloride, 1-methyl-4-[(methylphenylhydrazono)methyl]pyridinium methyl sulfate, Disperse Red 17, Basic Red 22, Basic Red 76, Basic Yellow 57, Basic Brown 16, Basic Brown 17, Disperse Black 9); azine-based dyes (e.g., Basic Blue 17, Basic Red 2); triarylmethane-based dyes (e.g., Basic Green 1, Basic Violet 3, Basic Violet 14, Basic Blue 7, Basic Blue 26, and those disclosed in EP 3034065 A1—which is incorporated herein by reference in its entirety; indoamine-based dyes (e.g., 2-β-hydroxyethylamino-5-[bis(β-4'-hydroxyethyl) amino]anilino-1,4-benzoquinone, 2-β-hydroxyethylamino-5-(2'-methoxy-4'-amino) anilino-1,4-benzoquinone, 3-N-(2'-chloro-4'-hydroxy) phenylacetamino-6-methoxy-1,4-benzoquinoneimine, 3-N-(3'-chloro-4'-methylamino)phenylureido-6-methyl-1,4-benzoquinoneimine, 3-[4'-N-(ethylcarbamylmethyl)amino] phenylureido-6-methyl-1,4-benzoquinoneimine); catechol-based dyes (e.g., purpurogallin, protocatechaldehyde); fluorescent dyes, such as those of the naphthalimide, cationic or non-cationic coumarin, xanthenodiquinolizine, azaxanthene, naphtholactam, azlactone, oxazine, thiazine, or dioxazine families, or polycationic fluorescent dyes of the azo, azomethine or methine families, for example those disclosed in US 2006/0005326—which is incorporated herein by reference in its entirety.

The dyestuff may also be a pigment, such as white or colored pigments, lakes, and pearlescent agents or flakes. Exemplary pigments include, but are not limited to, titanium dioxide, which may or may not be surface-treated, zirconium oxide, cerium oxide, iron oxide or chromium oxide, manganese violet, ultramarine blue, chromium hydrate, ferric blue, and organic pigments (e.g., nitroso-, xanthene-, quinolone-, phthalocyanin-, isoindolinone-, isoindoline-, quinacridone-perinone-, perylene-, diketopyrrolopyrrole-, thioindigo-, dioxazine-, and quinophthalone-based organic pigments).

Surfactant

The hair coloring composition of the present disclosure may include one or more surfactants, which may be non-ionic, amphoteric, anionic, or cationic surfactants, preferably nonionic surfactants, and may act as detergents, wetting agents, emulsifiers, foaming agents, and/or dispersants. The surfactant advantageously provides the hair coloring composition with good foamability and workability for ease of application, and may aid consistent application, coating, and delivery of the dyestuff to the hair follicles to provide the dyed hair with a long lasting, natural look, particularly when combined with the monosaccharide dyestuffs disclosed herein. The amount of surfactant present in the hair coloring composition may range from about 0.1 wt. %, preferably from about 0.5 wt. %, more preferably from about 1 wt. %, even more preferably from about 1.5 wt. %, yet even more preferably from about 2 wt. %, and up to about 10 wt. %, preferably up to about 5 wt. %, more preferably up to about 4.5 wt. %, even more preferably up to about 4 wt. %, yet even more preferably up to about 3 wt. %, based on the total weight of the hair coloring composition.

The hair coloring compositions preferably include at least one nonionic surfactant, such as an alkyl pyranoside; a polyoxyalkylene ether of a fatty alcohol, a polyol, or an ester; an ethylene oxide/propylene oxide copolymer; and/or a fatty amide.

Alkyl pyranoside surfactants are pyranose-based monosaccharides having a glycosidic bond to fatty alcohols having 6 to 26 carbon atoms, preferably 7 to 24 carbon atoms, more preferably 8 to 22 carbon atoms, even more preferably 9 to 20 carbon atoms, yet even more preferably 10 to 18 carbon atoms. The alkyl pyranoside may be formed by any combination of a pyranose-based monosaccharide, for example, allose, altrose, galactose, glucose, gulose, idose, mannose, and talose, as well as anhydro-, deoxy-, heteroatom-substituted-, or dehydro-variants thereof, with a fatty alcohol having 6 to 26 carbon atoms, either saturated or unsaturated, for example, 1-hexanol, 3-methyl-3-pentanol, 1-heptanol, 1-octanol, pelargonic alcohol, 1-decanol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, heneicosyl alcohol, behenyl alcohol, erucyl alcohol, lignoceryl alcohol, ceryl alcohol, as well as mixtures thereof (e.g., cetearyl alcohol, which is a mixture of cetyl and stearyl alcohols). Specific examples include, but are not limited to, hexyl glucoside, octyl glucoside, octyl galactoside, decyl glucoside, decyl galactoside, isodecyl glucoside, isoundecyl glucoside, lauryl glucoside, cetearyl glucoside, coco glucoside, and isotridecyl glucoside, as well as mixtures thereof, with decyl glucoside being the most preferred.

The surfactant may also be one or more non-ionic surfactants of the following types: a polyoxyalkylene ether of a fatty alcohol, for example, laureth-3, ceteareth-6, ceteareth-11, ceteareth-15, ceteareth-16, ceteareth-17, ceteareth-18, ceteareth-20, ceteareth-23, ceteareth-25, ceteareth-27, ceteareth-28, ceteareth-30, isoceteth-20, laureth-9/myreth-9, and PPG-3 caprylyl ether, as well as mixtures thereof, preferably ceteareth-25 is used; a polyoxyalkylene ether of a polyol (e.g., glycerin, glucose, sorbitol, etc.), specific examples include, but are not limited to, glycereth-7 caprylate/caprate, glycereth-2 cocoate, PEG-7 glyceryl cocoate, glycereth-7, glycereth-7-triacetate, glycereth-5-lactate, glycereth-7-diisononanoate, methyl gluceth-10, and polysorbates such as polysorbate-20, polysorbate-40, polysorbate-60, polysorbate-80; and/or a polyoxyalkylene ether of an ester exemplified by PEG-14 laurate, PEG-15 laurate, PEG-20 laurate, PEG-32 laurate, PEG-75 laurate, and PEG-150 laurate, including mixtures thereof.

Ethylene oxide/propylene oxide copolymers may also be included in the hair coloring compositions as nonionic surfactants, for example, PPG-12-buteth-16, PPG-3-buteth-5, PPG-5-buteth-7, PPG-7-buteth-10, PPG-9-buteth-12, PPG-12-buteth-16, PPG-15-buteth-20, PPG-20-buteth-30, PPG-28-buteth-35, and PPG-33-buteth-45.

Examples of fatty amides or polyoxyalkylene fatty amides which may be used as nonionic surfactants herein include, but are not limited to, cocoamide DEA, cocamide MEA, cocamide MIPA, cocamidopropylamine oxide, PEG-6 cocamide, trideceth-2 carboxamide MEA, PEG-4 rapeseedamide, and the like.

In preferred embodiments, the surfactant is a mixture of an alkyl pyranoside and a polyoxyalkylene ether of a fatty alcohol, for example in a weight ratio of from about 1:1, or from about 1.5:1, or from about 1.8:1, and up to about 3:1, or up to about 2:1. More preferably, the surfactant is a mixture of decyl glucoside and ceteareth-25, for example, in the above weight ratio ranges.

Amphoteric surfactants are preferably not included in the hair coloring composition, but when present, can be selected from imidazoline sulfonates, carboxylates, or phosphates (e.g., alkyl hydroxy ethyl imidazoline sulfonates, disodium lauroamphodiacetate, sodium lauroampho PG-acetate phosphate), amidosultaines (e.g., lauramidopropyl hydroxysultaine, cocamidopropyl hydroxysultaine, oleamidopropyl hydroxysultaine), betaines (e.g., cocamidopropylphosphobetaine, lauric/myristic pyrophosphobetaine, cocamidopropyl betaine), and the like, as well as mixtures of such materials.

The hair coloring compositions are preferably substantially free of anionic surfactants, however, when present, suitable anionic surfactants include, but are not limited to, sulfates of fatty alcohols or polyoxyalkylene ethers of fatty alcohols, phosphates of fatty alcohols or polyoxyalkylene ethers of fatty alcohols, sodium salts of fatty acids, acylamino acids, and lactylates. Specific examples of anionic surfactants that can be optionally included in the hair coloring compositions herein include, but are not limited to, sodium lauryl sulfate, sodium laureth sulfate, cetyl phosphate, sodium stearate, sodium behenoyl lactylate, sodium isostearoyl lactylate, sodium caproyl lactylate, sodium laureth-5 carboxylate, sodium laureth-6 carboxylate, sodium laureth-11 carboxylate, sodium stearate, dicetyl phosphate, ceteth-10-phosphate, sodium cocoyl taurate, sodium methyl cocoyl taurate, and sodium methyl oleoyl taurate.

The hair coloring compositions are preferably substantially free of cationic surfactants. However, in some embodiments, cationic surfactants are present, such as protonated fatty amines, that is, fatty amine salts derived from primary, secondary or tertiary fatty amines in combination with an acid. For example, protonated fatty amines of stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof Delivery Agent The hair coloring compositions of the present disclosure may include a delivery agent, which is a material capable of aiding the penetration of, and enhancing uniform delivery of, the dyestuff (and other components of the hair coloring composition) into the keratin fiber so that a deeper, longer-lasting, natural hair coloration can be achieved.

In preferred embodiments, the delivery agent is a dianhydrohexitol or a derivative thereof, which includes monoalkoxy substituted dianhydrohexitols and dialkoxy substituted dianhydrohexitols. Dianhydrohexitols (i.e., 1,4;3,6-dianhydrohexitols) are by-products of the starch industry most often obtained by dehydration of D-hexitols. These chiral biomass-derived products exist as three main isomers, namely isosorbide (I), isomannide (II), and isoidide (III), depending on the configuration of the two hydroxyl groups (derived from D-glucose, D-mannose, and L-fructose, respectively), and any of these isomers or derivatives of any of these isomers may be employed as the delivery agent herein, including mixtures.

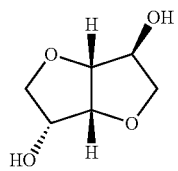

(I)

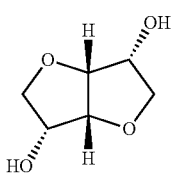

(II)

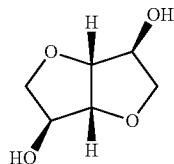

(III)

In preferred embodiments, a monoalkoxy substituted dianhydrohexitol or a dialkoxy substituted dianhydrohexitol is used, which is a dianhydrohexitol where one hydroxyl group is substituted to form an alkoxy group or a dianhydrohexitol where both hydroxyl groups are substituted to form two alkoxy groups (which can be the same or different), respectively. As used herein, "alkoxy" substitution includes straight chain, branched, cyclic, or (poly)oxyalkylene-type, alkoxy groups, either saturated or unsaturated, having up to 10 carbon atoms, preferably up to 8 carbon atoms, preferably up to 4 carbon atoms, for example 1 to 4 carbon atoms, and specifically includes: acyclic alkoxy groups such as methoxy, ethoxy, propoxy, allyloxy, isopropoxy, butoxy, isobutoxy, secondary butoxy, tertiary butoxy, pentoxy, isopentoxy, hexyloxy, heptyloxy, octyloxy, nonyloxy and decyloxy; cyclic alkoxy groups (having 3 to 10 carbon atoms) including cyclopropyloxy, cyclobutyloxy, cyclopentyloxy, cyclohexyloxy, and cycloheptyloxy groups; and (poly)oxyalkylene-type alkoxy groups such as polyoxyethylene (—O—(CH$_2$—CH$_2$—O)$_n$—R), polyoxypropylene (—O—(CH$_2$—CH(CH$_3$)—O)$_n$—R), and polyoxybutylene (—O—(CH$_2$—CH(CH$_2$CH$_3$)—O)$_n$—R) groups having up to 5 repeating units, i.e., n is from 1 to 5, wherein R is H or a C$_1$ to C$_3$ alkyl group (e.g., methyl, ethyl, n-propyl, isopropyl). Preferably, the delivery agent is a C$_1$ to C$_4$ monoalkoxy substituted dianhydrohexitol, or a C$_1$ to C$_4$ dialkoxy substituted dianhydrohexitol, most preferably a C$_1$ to C$_4$ dialkoxy substituted dianhydrohexitol. In the case of a dialkoxy substituted dianhydrohexitol, the carbon count refers to a total number of carbon atoms for each alkoxy substituent, and thus "a C$_1$ to C$_4$ dialkoxy substituted dianhydrohexitol" refers to compounds where each alkoxy substituent has 1 to 4 carbon atoms, independently of the other alkoxy substituent.

Examples of dianhydrohexitols or derivatives thereof suitable for use as delivery agents herein include, but are not limited to, isosorbide, isomannide, and isoidide, methyl isosorbide, dimethyl isosorbide, ethyl isosorbide, diethyl isosorbide, propyl isosorbide, dipropyl isosorbide, monoisopropyl isosorbide, diisopropyl isosorbide, methylethyl isosorbide, methylpropyl isosorbide, ethylpropyl isosorbide, butyl isosorbide, dibutyl isosorbide, isobutyl isosorbide, diisobutyl isosorbide, methylbutyl isosorbide, ethylbutyl isosorbide, propylbutyl isosorbide, methyl isomannide, methyl isoidide, dimethyl isomannide, and dimethyl isoidide. In preferred embodiments, the delivery agent is dimethyl isosorbide (a C$_1$ dialkoxy substituted dianhydrohexitol). In addition to aiding delivery of the dyestuff (and/or other components of the hair coloring composition), the unsubstituted and alkoxy substituted dianhydrohexitols disclosed herein are particularly advantageous because they are soluble in water, biologically harmless, and may enhance the health and appearance of hair follicles to which they are applied.

Other acceptable delivery agents that may be used as delivery agents in lieu of, or in addition to the dianhydrohexitols or derivatives thereof, include pyrrolidinone, caprylyl pyrrolidone, N-methylpyrrolidone, lauryl pyrrolidone, propylene carbonate, 2-benzyloxyethanol, gamma-butyrolactone, phenylethanol, diethyl glycol-monoethylether, polyethylene glycols (e.g., PEG-4, PEG-6, PEG-8, PEG-10, PEG-12, PEG-32), isopentyldiol, ethoxydiglycol, and the like, as well as mixtures thereof.

In some embodiments, the amount of delivery agent present in the hair coloring composition is from about 0.1 wt. %, preferably from about 0.5 wt. %, preferably from about 1 wt. %, preferably from about 1.5 wt. %, preferably from about 2 wt. %, and up to about 5 wt. %, preferably up to about 4 wt. %, preferably up to about 3 wt. %, preferably up to about 2.5 wt. %, based on a total weight of the hair coloring composition.

Solvent

In some embodiments, the hair coloring composition of the present disclosure is an aqueous composition or an oil-in-water (o/w) emulsion where the continuous phase is aqueous. Therefore, in preferred embodiments, the hair coloring composition further includes water in amounts of at least about 60 wt. %, more preferably at least about 65 wt. %, even more preferably at least about 70 wt. %, yet even more preferably at least about 75 wt. %, and up to about 95 wt. %, preferably up to about 90 wt. %, more preferably up to about 85 wt. %, even more preferably up to about 80 wt. %, based on a total weight of the hair coloring composition.

In addition to water, the hair coloring composition may optionally include at least one organic solvent which may aid solubilization of components not sufficiently soluble in water, adjust the surface properties of the hair coloring composition for enhanced workability, foamability, and/or foam stability, or to generally provide a medium suitable for the dyeing operation. The at least one organic solvent, may be chosen from, for example, a $C_1$ to $C_4$ lower alkanol, for example, methanol, ethanol (e.g., denatured alcohol), isopropanol, butanol; polyols and polyol ethers, for example, glycol, 1,3-propanediol, 1,3-butanediol, 2-butoxyethanol, propylene glycol, butylene glycol, hexylene glycol, isoprene glycol, diethylene glycol, dipropylene glycol, ethylene glycol monomethyl ether, ethylene glycol monoethyl ether, propylene glycol monomethyl ether, diethylene glycol monomethyl ether, diethylene glycol monoethyl ether, as well as mixtures thereof. Preferably, the organic solvent is ethanol. When present, the organic solvent may be included in the hair coloring compositions in an amount ranging from about 0.5 wt. %, preferably from about 1 wt. %, more preferably from about 1.5 wt. %, even more preferably from about 2 wt. %, yet even more preferably from about 2.5 wt. %, and up to about 10 wt. %, preferably up to about 5 wt. %, preferably up to about 4.5 wt. %, more preferably up to about 4 wt. %, even more preferably up to about 3.5 wt. %, yet even more preferably up to about 3 wt. %, based on a total weight of the hair coloring composition.

Preservative

The hair coloring composition may optionally further include a preservative. For example, the preservative may be selected to kill bacteria that might otherwise be sustained or multiplied in the composition, or to prevent degradation or chemical breakdown (e.g., oxidative degradation) of the composition. Preservatives suitable for use in cosmetic formulations are well-known to those skilled in the art. In this respect, the preservative chosen may be varied depending on the particular components present in the hair coloring composition. Illustrative of suitable preservatives include ethylparaben, propylparaben, methylparaben, EDTA or salts thereof (such as disodium EDTA), phenoxyethanol, DMDM hydantoin, benzyl alcohol, ethyldibromoglutaronitrile-phenoxyethanol/polyquatemium-7 (Euxyl K-400, Calgon), imidazolidinyl urea, diazolidinyl urea, benzalkonium chloride, benzethonium chloride, sodium benzoate, sorbic acid and the like, or combinations thereof. Preferably, the preservative is at least one of methylparaben, sodium benzoate, and benzyl alcohol, most preferably a mixture of these preservatives. When present, the preservative may be included herein in amounts of up to about 5 wt. %, preferably up to about 4 wt. %, preferably up to about 3 wt. %, preferably up to about 2 wt. %, preferably up to about 1 wt. %, for example from about 0.001 wt. % to about 3 wt. %, or 0.1 wt. % to about 2 wt. %, or 0.2 wt. % to about 1 wt. %, based on a total weight of the hair coloring composition.

Acidulant

The hair coloring compositions disclosed herein may be optionally formulated to include an acidulant for adjusting the pH to be more acidic/less alkaline. Additionally, depending on the chemical structure, the acidulant may act as a chelating agent and/or a buffering agent to neutralize minerals, enhance the activity of any preservatives present, and to stabilize active ingredients (e.g., the dyestuff). When the acidulant contains α-hydroxy acid functionality, the acidulant may also confer moisturizing and smoothing effects to the hair coloring composition.

When present, the acidulant may be included herein in amounts of up to about 5 wt. %, preferably up to about 4 wt. %, preferably up to about 3 wt. %, preferably up to about 2 wt. %, preferably up to about 1 wt. %, for example from about 0.001 wt. % to about 3 wt. %, or 0.02 wt. % to about 2 wt. %, or 0.1 wt. % to about 1 wt. %, or 0.2 wt. % to about 0.5 wt. %, based on a total weight of the hair coloring composition. The pH of the hair coloring composition may be varied, but is preferably less than 5, for example, at least 2, preferably at least 2.5, more preferably at least 3, even more preferably at least 3.5, and up to 5, preferably up to 4.5, more preferably up to 4.

The acidulant employed herein may be an inorganic acid or an organic acid, and specifically includes, but is not limited to, hydrochloric acid, orthophosphoric acid, sulfuric acid, carboxylic acids such as fumaric acid, acetic acid, and α-hydroxy acids such as tartaric acid, citric acid, and lactic acid, as well as mixtures thereof. Preferably citric acid is used.

Conditioning Agent

The hair coloring compositions of the present disclosure may also optionally include one or more conditioning agents, which may act as a moisturizer, emollient, occlusive agent, and/or humectant for the hair. Any suitable conditioning agent known to those of ordinary skill in the art may be employed herein. If included in the hair coloring composition, the amount of conditioning agent is typically less than about 15 wt. %, preferably less than about 10 wt. %, more preferably less than about 8 wt. %, or from about 0.1 wt. %, preferably from about 1 wt. %, more preferably from about 2 wt. %, even more preferably from about 4 wt. %, and up to about 10 wt. %, preferably up to about 8 wt. %, more preferably up to about 6 wt. %, even more preferably up to about 5 wt. %, based on a total weight of the hair coloring composition.

In preferred embodiments, the conditioning agent employed herein is a monomeric polyol, preferably a monomeric polyol having at least three hydroxyl groups (e.g., glycerin, erythritol, pentaerythritol, threitol, arabitol, xylitol, ribitol). In most preferred embodiments, the conditioning agent is glycerin. The hair coloring compositions may be substantially free of, or alternatively may include, retinyl palmitate, petrolatum, gelatin, guar hydroxypropyl trimonium chloride, natural botanicals and extracts thereof such as *Chamomile recutita, Sambucus nigra, Primula veris, Helianthus annuus, Urtica dioica* (i.e., nettle), *Olea europaea* (i.e., olive), aloe (e.g., barbadensis gel), kelp (e.g., sea kelp), phospholipids,), and the like, or combinations thereof.

In some embodiments, the hair coloring compositions are substantially free of conditioning agents of the following types: a quaternary ammonium compound, a fatty material (e.g., fatty alcohols, fatty acids, fatty hydrocarbon oils, and fatty esters), and a silicone. However, such conditioning agents may optionally be included herein. Suitable quaternary ammonium compounds include cetyltrimethylammonium chloride, behenyltrimethylammonium chloride, behentrimonium methosulfate, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (e.g., Arquad 2HT-75, available from Akzo Nobel), cocotrimethylammonium chloride, PEG-2-oleammonium chloride, and the like, as well as the corresponding bromides or hydroxides thereof.

Fatty materials which provide acceptable hair conditioning effects include fatty alcohols or corresponding carboxylic acids (i.e., fatty acid, for example, stearic acid), fatty hydrocarbon oils, and/or a fatty esters. Exemplary fatty alcohols have been listed previously, with preferred fatty alcohols being cetyl alcohol, stearyl alcohol, behenyl alcohol, and mixtures thereof (e.g., cetearyl alcohol). Fatty acids may include, but are not limited to, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid. Fatty hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and the like, as well as mixtures thereof. Branched-chain isomers of these compounds, as well as higher chain length hydrocarbons, can also be used. Suitable fatty esters are characterized by having at least one fatty aliphatic chain derived from a fatty acid, a fatty alcohol, or both. Fatty esters herein may be monoesters of the formula $R^1COOR^2$ in which at least one of $R^1$ and $R^2$ is an alkyl or alkenyl radical having 6 to 26 carbon atoms, preferably 7 to 24 carbon atoms, more preferably 8 to 22 carbon atoms, even more preferably 9 to 20 carbon atoms, yet even more preferably 10 to 18 carbon atoms, and where the sum of carbon atoms combined in $R^1$ and $R^2$ is from 7 to 52 carbon atoms, for example, cetyl octanoate and lauryl lactate. Diesters and triesters containing at least one fatty aliphatic portion can also be used. Particularly preferred fatty esters are mono-, di-, and tri-glycerides, more specifically the mono-, di-, and tri-esters of glycerol and at least one fatty acid, for example, glyceryl mono-, di-, or tri-stearate, cocoa butter, palm stearin, sunflower oil, soybean oil and coconut oil.

Suitable silicone conditioning agents are polydiorganosiloxanes, in particular polydimethylsiloxanes (dimethicones), polydimethylsiloxanes having hydroxyl end groups (dimethiconols), amino-functional polydimethylsiloxanes (amodimethicones), polyoxyalkylene functionalized polydimethylsiloxanes (dimethicone copolyols), and mixtures thereof. Exemplary silicones include cyclomethicone, phenyltrimethicone, alkyl dimethicone, fluorinated silicones, dimethicone, PEG-3 dimethicone, PEG-7 dimethicone, PEG-8 dimethicone, PEG-9 dimethicone, PEG-10 dimethicone, PEG-12 dimethicone, PEG-14 dimethicone, PEG-17 dimethicone, PEG/PPG-3/10 dimethicone, PEG/PPG-4/12 dimethicone, PEG/PPG-6/11 dimethicone, PEG/PPG-8/14 dimethicone, PEG/PPG-14/4 dimethicone, PEG/PPG-15/15 dimethicone, PEG/PPG-16/2 dimethicone, PEG/PPG-17/18 dimethicone, PEG/PPG-18/18 dimethicone, PEG/PPG-19/19 dimethicone, PEG/PPG-20/6 dimethicone, PEG/PPG-20/15 dimethicone, PEG/PPG-20/20 dimethicone, PEG/PPG-20/23 dimethicone, PEG/PPG-20/29 dimethicone, PEG/PPG-22/23 dimethicone, PEG/PPG-22/24 dimethicone, PEG/PPG-23/6 dimethicone, PEG/PPG-25/25 dimethicone and PEG/PPG-27/27 dimethicone, and the like, and combinations thereof Fragrance The hair coloring compositions of the present disclosure may be optionally formulated to include one or more fragrances known to those of ordinary skill in the cosmetics arts to impart a pleasant scent or to help mask any malodorous components that may be present in the hair coloring compositions. Non-limiting examples of compounds used as fragrances herein include dihydrocitronellyl nitrile, 2,2,6-trimethylcyclohexane carboxylic acid ethyl ester (i.e., Thesaron, available from Takasago International Corporation), 2-ethyl-4-(2,2,3-trimethyl-3-cyclopenten-1-yl)-2-buten-1-ol racemic or optically active form, preferably (E)-(R)-form (i.e., Levosandol, available from Takasago International Corporation), 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, 2-methyl-4-(2,2,3-trimethyl-3-cyclopenten-1-yl)-2-buten-1-ol racemic or optically active form, preferably (E)-(R)-form, tri(cis-3-hexenyl) orthoformate, 4-ethoxy-2-methyl-butanethiol, 5-methoxy-3-methyl-3-pentanethiol, thioglycerin, dibutyl sulfide, thiogeraniol, thiocineol, limonenethiol, 2-methyl-4-propyl-1,3-oxathian, 4-methoxy-2-methyl-2-butanethiol, terpene hydrocarbons such as p-cymene, terpinolene, myrcene, and β-caryophyllene, aldehydes such as heptanal, octanal, benzaldehyde, salicylic aldehyde, citronellal, α-hexylcinnamic aldehyde and lilial, esters such as methyl jasmonate, methyl dihydrojasmonate, γ-nonyllactone, γ-decalactone and coumarin, ethers such as anisole, p-cresyl methyl ether, β-naphthol methyl ether, and β-naphthol ethyl ether, ketones such as menthone, acetophenone, α-damascone, β-damascone, α-ionone, β-ionone, methyl ionone, irone, dihydrojasmone, cis-jasmone, muscone and civetone, alcohols such as cis-3-hexenol, heptanol, 2-octanol, benzyl alcohol, citronellol, geraniol, terpineol, tetrahydrogeraniol, anise alcohol, phenylethyl alcohol, phenoxy ethanol, santalol, sandalmysore core, bacdanol, ebanol, polysantol, and natural essential oils such as orange oil, lemon oil, lime oil, patchouli oil, cyprus oil, sandalwood oil, peppermint oil, spearmint oil, and anise oil, and the like, as well as mixtures thereof.

In some embodiments, the fragrance is present in amounts of up to about 3 wt. %, preferably up to about 2 wt. %, preferably up to about 1 wt. %, preferably up to about 0.5 wt. %, preferably up to about 0.3 wt. %, preferably up to about 0.2 wt. %, preferably up to about 0.1 wt. %, preferably up to about 0.01 wt. %, based on a total weight of the hair coloring composition.

Other Optional Ingredients

Various optional ingredients frequently used in topical formulations such as propellants, vehicles, adjuvants, anti-aging components, proteins, rheology control agents, dispersants, thickeners, film-forming agents, sequestering agents, cleansing agents, vitamins, botanicals, and sunscreen agents, as well as other classes of materials whose presence may be cosmetically, medicinally or otherwise desirable, can also optionally be included at their conventional art-established usage levels. In preferred embodiments, the hair coloring compositions are substantially free of such optional ingredients, however, when included, non-limiting examples which can be used include film-forming and moisturizing materials such as hydrolyzed wheat protein/wheat oligosaccharides (e.g., Cropeptide W by Croda Inc.), hydrolyzed corn protein, hydrolyzed wheat gluten, hydrolyzed yeast protein, hydrolyzed vegetable protein, hydrolyzed soy protein, hydrolyzed rice protein, and hydrolyzed potato protein; cleansing agents and emollients such as polyethylene glycol derivatives of castor oil, for example, PEG-40 castor oil (Surfactol 365, available from Vertellus), PEG-45 castor oil, PEG-50 castor oil, PEG-60 castor oil, and PEG-100 castor oil; sunscreens or UV light absorbing compounds octyldimethyl PABA, benzophenone-4, DEA methoxycinnamate, 2-phenyl-benzimidazole-5-sulfonic acid, and triethanolamine salicylate; thickeners such as carbomer and $C_{10}$-$C_{30}$ alkylacrylate cross-polymer; film forming polycationic polymers such as polyquaternium-1, polyquaternium-2, polyquaternium-4, polyquaternium-5, polyquaternium-6, polyquaternium-7, polyquaternium-8, polyquaternium-9, and polyquaternium-10; and thickening agents such as modified cellulose polymers, for example, hydroxyethyl cellulose and methyl cellulose.

In preferred embodiments, the hair coloring composition includes 5 to 10 wt. % of a first monosaccharide having 2 to 4 carbon atoms (e.g., dihydroxyacetone), 0.001 to 0.5 wt. % of a second monosaccharide having 2 to 4 carbon atoms (e.g., erythrulose); 0.1 to 3 wt. % of a surfactant, which is a mixture of an alkyl pyranoside (e.g., decyl glucoside) and a polyoxyalkylene ether of a fatty alcohol (e.g., ceteareth-25); 0.1 to 1 wt. % of a delivery agent, which is a $C_1$ to $C_4$ dialkoxy substituted dianhydrohexitol (e.g., dimethyl isosorbide), and 70 to 85 wt. % water, with the balance optionally including one or more of an organic solvent (e.g., ethanol), a preservative (e.g., a mixture of methylparaben, sodium benzoate, and benzyl alcohol), an acidulant (e.g., citric acid), a conditioning agent (e.g., glycerin), and/or a fragrance.

In preferred embodiments, the hair coloring composition includes 5 to 10 wt. % of a first monosaccharide having 2 to 4 carbon atoms (e.g., dihydroxyacetone), 0.001 to 0.5 wt. % of a second monosaccharide having 2 to 4 carbon atoms (e.g., erythrulose); 0.1 to 3 wt. % of a surfactant, which is a mixture of an alkyl pyranoside (e.g., decyl glucoside) and a polyoxyalkylene ether of a fatty alcohol (e.g., ceteareth-25); 0.1 to 1 wt. % of a delivery agent, which is a $C_1$ to $C_4$ dialkoxy substituted dianhydrohexitol (e.g., dimethyl isosorbide), 70 to 85 wt. % water, 1 to 3 wt. % of an organic solvent (e.g., ethanol), 0.001 to 0.3 wt. % of a preservative, which is a mixture of methylparaben, sodium benzoate, and benzyl alcohol, 0.001 to 0.2 wt. % of an acidulant (e.g., citric acid), 3 to 7 wt. % of a conditioning agent, which is a monomeric polyol having at least three hydroxyl groups (e.g., glycerin), and 0.01 to 0.5 wt. % of a fragrance.

The hair coloring compositions herein can be prepared by any method known to those of ordinary skill in the art. By way of example, the hair coloring composition may be prepared by (i) mixing together all water soluble components in an appropriately sized vessel with water with optional heating (e.g., 40 to 90° C., preferably 50 to 80° C., more preferably 60 to 70° C.) and stirring until homogenous, (ii) in a separate vessel, mixing all oil phase ingredients, if any, with optional heating (e.g., 40 to 100° C., preferably 50 to 90° C., more preferably 60 to 80° C.) and stirring until homogeneous, (iii) mixing together the homogenous mixture from (i) with the homogenous mixture from (ii), if any, with optional heating (e.g., 40 to 100° C., preferably 50 to 90° C., more preferably 60 to 80° C.) and stirring to form the hair coloring composition.

Alternatively, the hair coloring composition may be prepared by (i) mixing together all water soluble components except for the dyestuff component (e.g., the first and second monosaccharides having 2 to 4 carbon atoms) in an appropriately sized vessel with water with optional heating (e.g., 40 to 90° C., preferably 50 to 80° C., more preferably 60 to 70° C.) and stirring until homogenous, (ii) in a separate vessel, mixing all oil phase ingredients, if any, with optional heating (e.g., 40 to 100° C., preferably 50 to 90° C., more preferably 60 to 80° C.) and stirring until homogeneous, (iii) mixing together the homogenous mixture from (i) with the homogenous mixture from (ii), if any, with optional heating (e.g., 40 to 100° C., preferably 50 to 90° C., more preferably 60 to 80° C.) and stirring until a homogenous aqueous composition or uniform oil in water emulsion is formed, and (iv) adding the dyestuff component (e.g., the first and second monosaccharides having 2 to 4 carbon atoms) to the homogenous aqueous composition or uniform oil in water emulsion, once the homogenous aqueous composition or uniform oil in water emulsion has cooled to 40° C. or below, and stirring under conditions similar to above, to form the hair coloring composition.

Once cooled, the hair coloring composition produced by either method may then be packaged, for example in a non-aerosol foam generating dispenser, for sale and/or distribution.

Properties

The hair coloring compositions of the present disclosure are stable for up to 4 years, for example from 24 months to 36 months, at room temperature or at sub-ambient temperatures without significant/rapid degradation of the active components or ingredient precipitation, which is known to sometimes occur with hair coloring compositions. The hair coloring compositions are thus suitable for long-term storage, distribution, and storage in between uses.

The hair coloring compositions disclosed herein have acceptable viscosity and surface tension in a liquid state, which allows for facile processing, workability (e.g., foamability), and packaging, and provides suitable foam characteristics once converted into a foam.

The viscosity of the hair coloring composition (as a liquid at 25° C.) is typically from about 1 mPa·s, preferably from about 2 mPa·s, more preferably from about 3 mPa·s, more preferably from about 5 mPa·s, even more preferably from about 10 mPa·s, yet even more from about 20 mPa·s, and up to about 300 mPa·s, preferably up to about 200 mPa·s, more preferably up to about 100 mPa·s, even more preferably up to about 50 mPa·s, yet even more preferably up to about 30 mPa·s. It is to be noted that the viscosity as referred to herein refers to a value obtained after rotating the liquid mixture at 60 rpm for one minute at 25° C. by a B-type rotational viscometer (model TV-10), manufactured by TOKYO KEIKI INC., with rotor No. 1 or 2. When the object to be measured has a viscosity of less than 100 mPa·s, the viscosity is measured using rotor No. 1, whereas when it has a viscosity of 100 to 499 mPa·s, the viscosity is measured using rotor No. 2. Measurement is made in a thermostat bath at 25° C. immediately after mixing, and temperature fluctuations caused by heat of reaction are negligible.

In preferred embodiments, the hair coloring composition is foamable and is in the form of a foam when applied. The stability of foam depends upon an interaction between the foam and an interface between foams. The foam bursts as a liquid film becomes thinner from flowing downward due to gravity or as liquid generally flows due to curvature differences of the foam. If the thickness of the liquid film is in the range of about 5 to 15 nm, the liquid film cannot resist the pressure from the inside to burst. In general, foams generated from aqueous solutions lack repulsive forces of an electric double layer in a liquid film, have low stability by hydration, and low resistance against liquid film thinning due to gravitational/curvature effects, leading to poor foam stability. However, the addition of one or more surfactants in an appropriate amount lowers the surface tension thereby accelerating foam formation, maintaining liquid film thickness for longer periods of time, and delaying gravitational/curvature breakdown effects. Thus, the present inventors have discovered that the hair coloring compositions herein, in addition to providing desirable hair dyeing results, are also capable of being foamed into easily-applied and stable foams that resist dripping (i.e., conversion back into a liquid state) to aid hair application while preventing staining of the skin (e.g., the scalp). In preferred embodiments, the foams generated from the hair coloring compositions disclosed herein are continuously retained for at least 1 minute, preferably at least 2 minutes, more preferably at least 10 minutes, and up to 50 minutes.

Method for Coloring Hair

The present disclosure provides a method for coloring hair by applying the hair coloring composition, in one or more embodiments, onto the hair. In order to achieve an acceptable amount of coloration, a person who desires such coloration can apply evenly an effective amount of the hair coloring composition for an effective application time over an entire treatment area (e.g., total coverage of gray hair), or to particularly problematic spots (e.g., gray hair located on the side of the head or sideburns). Thus, the hair coloring compositions can be applied for subtle changes in hair color such as gray hair blending, or more dramatic effects such as total gray hair coverage. Further, the method herein produces natural looking dyed hair, and after dyeing, provides excellent fastness to shampooing, irrespective of the kind of shampoo used for shampooing. In hair coloring applications, the steadfastness of the color (i.e., the resistance to color fading after washing) is of greater importance than in skin coloring/tanning applications, since dyed hair is likely to be exposed to a greater number of washings per dyeing application when compared to dyed skin as skin cells are shed and renewed at a higher rate and thus have a lower life cycle than hair follicles.

In a typical method, the hair coloring compositions as described above are topically applied to wet or dry hair. Preferably, the hair coloring compositions are applied to freshly shampooed and dried hair. The hair coloring compositions may be used as a single treatment to color the hair or applied in a progressive manner so that the hair color becomes more intense on subsequent applications until a desired coloration is reached. To avoid staining of skin, the hair coloring compositions may be applied with gloves or with a spreading instrument such as a comb or brush. Preferably, the hair coloring composition is applied uniformly to each hair fiber, from the root to the end of the hair fiber.

The effective application time may range from 1 minute, preferably from 3 minutes, more preferably from 5 minutes, even more preferably from 10 minutes, and up to 60 minutes, preferably up to 50 minutes, more preferably up to 40 minutes, even more preferably up to 30 minutes, yet even more preferably up to 20 minutes, depending on whether or not heat is applied. Application times outside of these ranges may also be used to vary the degree of coloration, as desired.

In preferred embodiments, the hair coloring compositions herein are applied to the hair in the form of a foam. Foam hair coloring compositions are easy to apply (for both complete coverage or for targeting problematic spots), and also help prevent unwanted staining of the skin and scalp that can be problematic with sprays and other topical forms, for example, by reducing the propensity of the compositions to drip. Any foaming method known to those of ordinary skill in the cosmetics arts can be used for foaming the hair coloring compositions of the present disclosure, but preferably a non-aerosol foam generating dispenser is used for discharging the hair coloring compositions as a foam. A non-aerosol foam generating dispenser is a device which is used to discharge the hair coloring composition in the form of a foam by mixing it with air without using a propellant, for example a dispenser actuated by manual mechanical pumping.

In preferred embodiments, the method further involves applying heat to the hair at a dyeing temperature of 30 to 205° C. It has been surprisingly found that heat speeds up the color development with exemplary effective application times of less than 20 minutes, preferably less than 10 minutes, more preferably less than 5 minutes, and produces dyed hair with a deeper, richer color than colors produced in the absence of applied heat.

In some embodiments, heat is applied by use of a hair dryer/blow dryer, for example, to achieve a dyeing temperature of from about 30° C., preferably from about 35° C., more preferably from about 40° C., and up to about 60° C., preferably up to about 55° C., more preferably up to about 50° C., even more preferably up to about 45° C. Therefore, common commercial/household hair dryers/blow dryers may be used as they would for normal operation for applying heat in the methods herein. While hair dryers or blow dryers capable of producing high temperatures (i.e., dyeing temperatures above 60° C.) may also be used, it is often difficult to apply high heat to hair in this fashion without burning the scalp. Therefore, in some embodiments, a hair iron (e.g., a straight iron, a curling iron, etc.) is used to apply high temperatures, that is, dyeing temperatures of more than 60° C., preferably more than 70° C., preferably more than 80° C., preferably more than 90° C., preferably more than 100° C., preferably more than 110° C., preferably more than 120° C., preferably more than 130° C., and up to 205° C., preferably up to 200° C., preferably up to 190° C., preferably up to 180° C., preferably up to 170° C., preferably up to 160° C., preferably up to 150° C., preferably up to 140° C. Thus, common commercial/household hair irons may be used as they would for normal operation for applying high heat in the methods herein.

In some embodiments, after application of the hair coloring composition, and any optional heating, the hair is simply allowed to dry. In some embodiments, after application of the hair coloring composition, and after optional application of heat, the hair is rinsed and/or washed with shampoo to remove the hair coloring composition. Preferably, the hair coloration fully develops during the application process and prior to rinsing/washing, particularly when heat is applied. However, in some instances the color may continue to develop slightly, even after the hair coloring composition is removed by rinsing or shampooing.

Even with the application of high heat, the methods herein are mild and do not damage keratin fibers during the dyeing process. To this end, it is preferable that the methods herein do not require the use of harsh chemicals, such as oxidizing agents, either together with the hair coloring compositions, or as a separate application. Oxidizing agents conventionally used for oxidative dyeing of keratin fibers are, for example, peroxides (e.g., hydrogen peroxide, benzyl peroxide, urea peroxide, etc.), bleaching agents (e.g., chlorine dioxide, hypochlorite, etc.), alkali metal bromates (e.g., sodium bromate), persalts such as perborates (e.g., sodium perborate) and persulfates (e.g., potassium persulfate), peracids (e.g., peracetic acid, pernonoic acid, nonylamidoperoxycaproic acid (NAPCA)), and oxidase enzymes such as peroxidases, 2-electron oxidoreductases (e.g., uricases) and 4-electron oxygenases (e.g., laccases). Preferably, the water used to wet and/or rinse the hair, either before or after application of the hair coloring composition, also contains less than 1 ppm of oxidizing agents (e.g., chlorine dioxide, hypochlorite, etc.), preferably less than 50 ppb.

When one or more monosaccharides having 2 to 4 carbon atoms are employed as the dyestuff in the hair coloring composition, a two-component application system or "kit" is also envisioned which includes 1) the hair coloring composition comprising the monosaccharide(s) having 2 to 4 carbon atoms as discussed above, and 2) an amino acid composition configured to drive the Maillard reaction to increase the speed of color formation and/or to produce certain color tones in reaction with the monosaccharide from the first component. These two components may be part of an application kit and stored in separate containers.

The amino acid composition may comprise any amino acid, but preferably includes one or more natural amino acids (i.e., 21 proteinogenic α-amino acids), most preferably one or more of serine, glycine, alanine, and glutamic acid. In preferred embodiments, the amount of amino acid(s) in the second component applied to the hair is at least 10 wt. %, preferably at least 20 wt. %, preferably at least 30 wt. %, preferably at least 40 wt. %, more preferably at least 50 wt. %, even more preferably at least 60 wt. %, yet even more preferably at least 70 wt. %, yet even more preferably at least 80 wt. %, and up to 100 wt. %, based on the total weight of monosaccharide(s) having 2 to 4 carbon atoms applied to the hair from the first component. The type of amino acid and the amount of amino acid present in the amino acid composition may be adjusted to vary the color produced.

In addition to the amino acid(s), the amino acid composition may include water and optionally a surfactant, a delivery agent, an organic solvent, a preservative, an acidulant, a conditioning agent, a fragrance, and/or any other various ingredients disclosed herein in amounts similar to that of the hair coloring composition. In preferred embodiments, like the hair coloring composition, the amino acid composition is an aqueous mixture capable of being foamed for ease of application.

To use the two-component application system, the amino acid composition may be mixed with the hair coloring composition of the disclosure at the time of use and the combined mixture may then be immediately applied to the hair. Alternatively, the amino acid composition is not premixed with the hair coloring composition. Instead, the two components are applied sequentially without intermediate rinsing, whereby the hair coloring composition is applied first followed by application of the amino acid composition (or vice versa, that is, the amino acid composition is applied first followed by application of the hair coloring composition). Following application of both the hair coloring composition and the amino acid composition, heat may then be applied at a dyeing temperature of 30 to 205° C. to speed the color formation and produce a deeper, richer color as discussed previously.

The examples below are intended to further illustrate radiation curable inkjet inks and surface roughness properties and are not intended to limit the scope of the claims.

EXAMPLES

Example 1

Example Hair Coloring Composition

| INCI Name | RM in Finished Product % wt./wt. |
| --- | --- |
| Water | 73.418 |
| Glycerin | 5.00 |
| Methylparaben | 0.20 |
| Sodium Benzoate | 0.001 |
| Ceteareth-25 | 0.40 |
| Citric Acid | 0.02 |
| Decyl Glucoside (55%) | 0.75 |
| Dimethyl Isosorbide | 0.25 |
| Fragrance | 0.20 |
| Water | 11.00 |
| Erythrulose (80%) | 0.01 |
| Dihydroxyacetone | 6.25 |
| Alcohol Denat. | 2.50 |
| Benzyl Alcohol | 0.001 |

INCI = International Nomenclature of Cosmetic Ingredients
RM = raw material

To prepare the hair coloring composition of Example 1, water and glycerin are added to a large vessel and heated to 75° C. Additional water soluble ingredients are added and mixed until homogenous. The mixture is cooled to 40° C. In a separate vessel dihydroxyacetone and erythrulose are mixed until clear. This premix is added to the large vessel and mixed for 15 minutes.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A hair coloring composition, consisting of:
from 5 to 25 wt. % of a first monosaccharide having 2 to 4 carbon atoms;
from 0.001 to 10 wt. % of a second monosaccharide having 2 to 4 carbon atoms;
from 0.1 to 5 wt. % of a surfactant, wherein said surfactant is a mixture of decyl glucoside and ceteareth-25;
from 0.1 to 0.5 wt. % of a delivery agent, wherein said delivery agent is dimethyl isosorbide; and from 0.001 to 3 wt % of a preservative;
from 60 to 90 wt % of water;
from 0.5 to 5 wt. % of an organic solvent;
from 0.001 to 3 wt. % an acidulant;
from 1 to 10 wt. % of a conditioning agent; and
1 wt. % or less of a fragrance;
each based on a total weight of the hair coloring composition.

2. The hair coloring composition of claim 1, wherein the first monosaccharide is dihydroxyacetone.

3. The hair coloring composition of claim 1, wherein the second monosaccharide is erythrulose.

4. The hair coloring composition of claim 1, wherein a weight ratio of the first monosaccharide to the second monosaccharide is 10:1 to 1,000:1.

5. The hair coloring composition of claim 1, which has a pH of from 2 to 5.

6. The hair coloring composition of claim 1, Wherein the conditioning agent is glycerin.

7. The hair coloring composition of claim 1, which is in the form of a foam.

8. A method fix coloring hair, comprising:
applying a hair coloring composition onto the hair, wherein the hair coloring composition consists of:
from 5 to 25 wt. % of a first monosaccharide having 2 to 4 carbon atoms;
from 0.001 to 10 wt. % of a second monosaccharide having 2 to 4 carbon atoms;
from 0.1 to 5 wt % of a surfactant, wherein said surfactant is a mixture of decyl glucoside and ceteareth-25;
from 0.1 to 0.5 wt. % of a delivery agent, wherein said delivery agent is dimethyl isosorbide; and
from 0.001 to 3 wt % of a preservative, wherein the preservative comprises a mixture of sodium benzoate and benzyl alcohol;
from 60 to 90 wt. % of water;
from 0.5 to 5 wt. % of an organic solvent;
from 0.001 to 3 wt. % of an acidulant;
from 1 to 10 wt. % of a conditioning agent; and
1 wt. % or less of a fragrance;
each based on a total weight of said hair coloring composition.

9. The method of claim 8, further comprising applying heat to the hair at a dyeing temperature of from 30° C. to 205° C.

10. The method of claim 9, wherein the dyeing temperature is from 30° C. to 60° C.

11. The method of claim 9, wherein the dyeing temperature is from more than 60° C. to 205° C.

12. The method of claim 8, wherein the hair coloring composition is in the form of a foam.

13. The method of claim 8, wherein the hair coloring composition is not applied to skin.

14. The hair coloring composition of claim 1, wherein the first monosaccharide is dihydroxyacetone and the second monosaccharide is erythrulose.

15. The hair coloring composition of claim 1, wherein the amount of dimethyl isosorbide is 0.25 wt %.

16. The hair coloring composition of claim 1, wherein the preservative comprises a mixture of sodium benzoate and benzyl alcohol.

17. The hair coloring composition of claim 1, wherein a weight ratio of the first monosaccharide to the second monosaccharide is from 200:1 to 1,000:1.

18. The method of claim 8, further comprising applying heat to the hair at a dyeing temperature of from 45° C. to 205° C.

19. The method of claim 8, further comprising applying heat to the hair at a dyeing temperature of from 45° C. to 60° C.

* * * * *